United States Patent
Chen

(10) Patent No.: US 12,010,996 B2
(45) Date of Patent: Jun. 18, 2024

(54) TRIS-SUBSTITUTED BIGUANIDE COMPOUNDS AND THEIR USES

(71) Applicant: Hwang Hsing Chen, Allen, TX (US)

(72) Inventor: Hwang Hsing Chen, Allen, TX (US)

(*) Notice: Subject to any disclaimer, the term of this patent is extended or adjusted under 35 U.S.C. 154(b) by 669 days.

(21) Appl. No.: 17/292,386

(22) PCT Filed: Nov. 8, 2019

(86) PCT No.: PCT/US2019/060577
§ 371 (c)(1),
(2) Date: May 7, 2021

(87) PCT Pub. No.: WO2020/097536
PCT Pub. Date: May 14, 2020

(65) Prior Publication Data
US 2022/0015366 A1  Jan. 20, 2022

Related U.S. Application Data

(60) Provisional application No. 62/766,879, filed on Nov. 8, 2018.

(51) Int. Cl.
*A01N 47/44* (2006.01)

(52) U.S. Cl.
CPC .................. *A01N 47/44* (2013.01)

(58) Field of Classification Search
CPC ......... A01N 47/44; A01N 33/04; A01N 47/42
USPC .......................................... 424/49, 401, 405
See application file for complete search history.

(56) References Cited

U.S. PATENT DOCUMENTS

| | | |
|---|---|---|
| 2002/0122831 A1 | 9/2002 | Mowrey-McKee |
| 2013/0040924 A1 | 2/2013 | Whiteford |
| 2014/0221318 A1 | 8/2014 | Yin |

OTHER PUBLICATIONS

PCT/US2019/060577—International Search Report and Written Opinion dated Mar. 3, 2020.

*Primary Examiner* — Walter E Webb
(74) *Attorney, Agent, or Firm* — Law Office of Jeff Williams PLLC; J. Oliver Williams

(57) ABSTRACT

Novel tris-substituted biguanide compounds are made by reaction of sodium dicyanamide with a trifunctional primary amine followed by reaction with anilines. The tris-substituted biguanide compounds are potent biocide and useful as a disinfectant. The novel compounds have biocidal activity comparable to those of widely used chlorhexidine with respect to width of antibacterial spectrum and in immediate effectiveness. The novel tris-substituted biguanide compounds can also be used for cleaning wounds, preventing dental plaque, treating yeast infections of the mouth, and to keep urinary catheters from blocking, These novel compounds have superior aqueous solubility and bioavailability and have potent antibacterial activity especially against *A. baumanni* and *K. pneumonia*.

14 Claims, No Drawings

US 12,010,996 B2

TRIS-SUBSTITUTED BIGUANIDE COMPOUNDS AND THEIR USES

TECHNICAL FIELD

The present invention relates to novel tris-substituted biguanide compounds. The tris-substituted biguanide are made by condensation of sodium dicyanamide and a trifunctional primary amine and then reaction with substitute anilines hydrochloride. Alternately the tris-substituted biguanide can also be made by condensation of substitute anilines hydrochloride and sodium dicyanamide and then reaction with a trifunctional primary amine. The preferred trifunctional primary amines include propane-1,2,3-triamine, pentane-1,3,5-triamine, N/N-bis(2-aminoethyl)-ethane-1,2-daiamine, $N^2,N^4,N^6$-tris(6-aminohexyl)-1,3,5-triazine-2,4,6-triamine, $N^2,N^4,N^6$-tris(6-aminopropyl)-1,3,5-triazine-2,4,6-triamine, $N^2,N^4,N^6$-tris(6-aminobutyl)-1,3,5-triazine-2,4,6-triamine, $N^2,N^4,N^6$-tris(6-aminoheptyl)-1,3,5-triazine-2,4,6-triamine, $N^2,N^4,N^6$-tris(6-aminopentyl)-1,3,5-triazine-2,4,6-triamine.

The tris-substituted biguanide compounds exhibit higher biocidal efficacy than widely used chlorhexidine especially against *Pseudomonas aeruginasa* presumably because of the better surface coverage of the microorganisms. The tris-substituted biguanide compounds exhibit higher molecular weight as compared to known bis-biguanide compounds and have higher biocidal efficacy. The tris-substituted biguanide compounds have an amino group that can enhance its solubility without additional salts as compared to the widely used chlorhexidine. The higher MW tris-substituted biguanide compounds are safe for the eyes and skin, and have a lower adsorption onto contact lenses and suitable for ophthalmic and cosmetic uses.

DESCRIPTION OF THE PRIOR ART

A biocide is a chemical substance, which can deter, render harmless, or exert a controlling effect on any harmful organism. Biocides are commonly used in medicine, agriculture, forestry, and industry.

The development of new and useful biocides requires consideration of many elements such as the following: the type of organism whose control is desired; the manner in which the biocide is to be deployed; the costs of preparing and delivering the biocide; environmental or disposal issues; and so on. Depending on the potential use envisioned, primary considerations are likely to include both its potency against the organisms targeted, as well as its biocompatibility, e.g. lack of toxicity against the humans or animals which may come into contact with it. Biocides may have a broad or narrow spectrum of activity.

Many of the current organic biocides have two functional group components, a hydrophilic/polar part and a hydrophobic/oil part. Broad-spectrum biocides may require higher hydrophobic elements in order to penetrate biological membranes and achieve their full potency. Hydrophobicity in biocides can be achieved through incorporation of long chain hydrocarbons or aryl groups into the structure of the molecule. However, the current organic biocides used in the pharmaceutical field are focused on improving biocompatibility to reduce the toxicity against human tissues.

Discovery of biocides with a desired balance between hydrophilicity and hydrophobicity for its field of use is important and highly challenging.

The present invention relates to but different from chlorhexidine that is a bis-biguanide compound developed in 1954 as a disinfectant. Chlorhexidine exhibits disinfecting or germicidal activities on a wide range of general bacteria and is widely used because of its quick effect and low toxicity. Especially, it is used as a gluconate salt, which has high solubility in water, for disinfection of hands and fingers in hospitals, body skin to be operated on, and medical instruments, particularly surgical instruments.

However, chlorhexidine has a defect that it is less effective against some Gram-negative bacteria, especially *Pyocyaneus* bacilli, typical of which is *Pseudomonas aeruginosa*. Furthermore, recently *Pyocyaneus bacillus* strains and *Pseudomonas cepacia* strains, which are resistant to this disinfectant, have been reported to be a problem in medical institutions. Chlorhexidine sometimes causes shock symptoms when it is administered to mucous membranes in a conventional concentration. Therefore, administration thereof to mucous membranes other than conjunctivae is now prohibited.

Under these circumstances, a substitute for chlorhexidine which retains the wide antibacterial spectrum of chlorhexidine and possesses germicidal effect and medial applicability superior to that of chlorhexidine has been sought. Thus, there is a demand for a novel chlorhexidine-type disinfectant for medical use which can be used in a concentration low enough to be safely applicable to mucous membranes, has improved germicidal activity especially against *Pyocyaneus bacillus* strains, against which chlorhexidine is no longer effective, and is suitable for use as a topical disinfectant for surgical operations.

For example, U.S. Pat. No. 5,420,350 discloses a novel bis-biguanide compound with a different substitute of the phenyl group by replacing a chloro group with trifluoromethoxyl group that enhances its antibacterial effectiveness especially against *Pseudomonas* aeruginasa.

U.S. 2012/0148530 discloses polybiguanide-based compounds for the treatment or prevention of virus infection. A number of end cap modifications for polybiguanide compounds are disclosed.

WO 2012/047,630 discloses compositions, methods to prevent, inhibit bacterial infection, HIV infection including "non-substituted terminal biguanides" derived from diamines, triamines, or polyamines.

US2014/0073631 discloses guanidine and biguanidine derivatives which have antiviral and antimicrobial activity. The derivatives consist a linear or branched backbone with ending guanidine or biguanidine groups that are connected with groups consisting of an antibacterial agent, an antibiotic, a quinolone, or an azaquinolone.

U.S. Pat. No. 2,368,647 discloses light sensitive photographic materials including di, tris, or poly "non-substituted terminal buguanides".

U.S. Pat. Nos. 8,440,212, 7,951,387, 6,503,952, 6,303,557, 6,010,687, 5,922,693, 5,885,562, 5,668,084, 5,529,713, 5,470,875, 5,356,555, and 5,141,803 disclose compositions consisting of polyhexamethylene biguanide for antimicrobial, wound dressing, cleaning and deodorant uses.

However, polyhexamethylene biguanide is known to be irritating to ocular tissues. All of the prior art are related to tris-unsubstituted biguande compounds and bis-biguanide and but none of tris-substituted biguanide compounds are disclosed. There still exists a need for biocides with useful antimicrobial activity; non-irritating; low toxicity; compatibility with the materials and tissue with which they come into contact.

SUMMARY OF THE INVENTION

The present invention is directed to tris-substituted biguanide compounds. In particular, this invention relates to novel tris-substituted biguanide compounds, which have three substituted biguanide groups connected to a three-point linker to form 2-dimensional compounds for the maximal surface coverage of the microorganisms to enhance antimicrobial efficacy. The present invention also relates to the use of these compounds as biocide in the industry, especially in pharmaceutical, cosmetic and lens care products. In particular, the present invention relates to the use of these new compounds as preservatives for ophthalmic, otic, cosmetic or nasal compositions and as disinfectants for contact lens care products.

The compounds of the present invention differ from prior compounds through the introduction of an extra biguanide group. Without wishing to be bound by theory, it is thought that the tris-substituted biguanide groups may increase antimicrobial efficacy by maximal surface coverage with the two-dimensional conformation and enhance ocular comfort by minimum uptake and release on contact lenses. Other features and advantages of the invention will become apparent from the following detailed description and claims.

BRIEF DESCRIPTION OF THE DRAWINGS

The novel biocides of this invention comprise a compound having three substituted biguanide groups of the following formula:

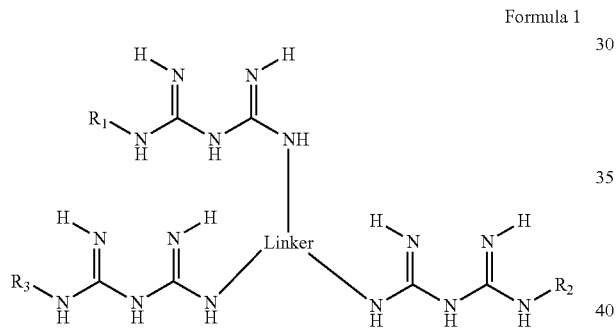

Formula 1 wherein Linker represent linkage group with 3, or more points of connections for biguanide groups and; R1, R2, R3 represent independently the same or different alkyl, aryl or heterocyclic groups, optionally substituted with halogen, O—R4, N—R5R6, R7; R4, R5, R6, R7 represent independently the same or different alkyl or aryl groups, optionally substituted with halogen, O-alkyl.

The preferred biocides of the present invention comprise a tris-substituted biguanide compound of the following formula:

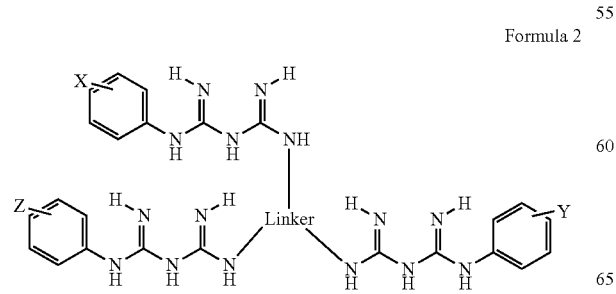

Formula 2 wherein Linker represent linkage group with 3, or more points of connections for biguanide groups and; X, Y, Z represent independently the same or different alkyl, O-alkyl, aryl or O-aryl groups, optionally substituted with halogen, O—R4, N—R5R6, R7; R4, R5, R6, R7 represent independently the same or different alkyl or aryl groups, optionally substituted with halogen, O-alkyl; linker represents linkage groups of the following structures:

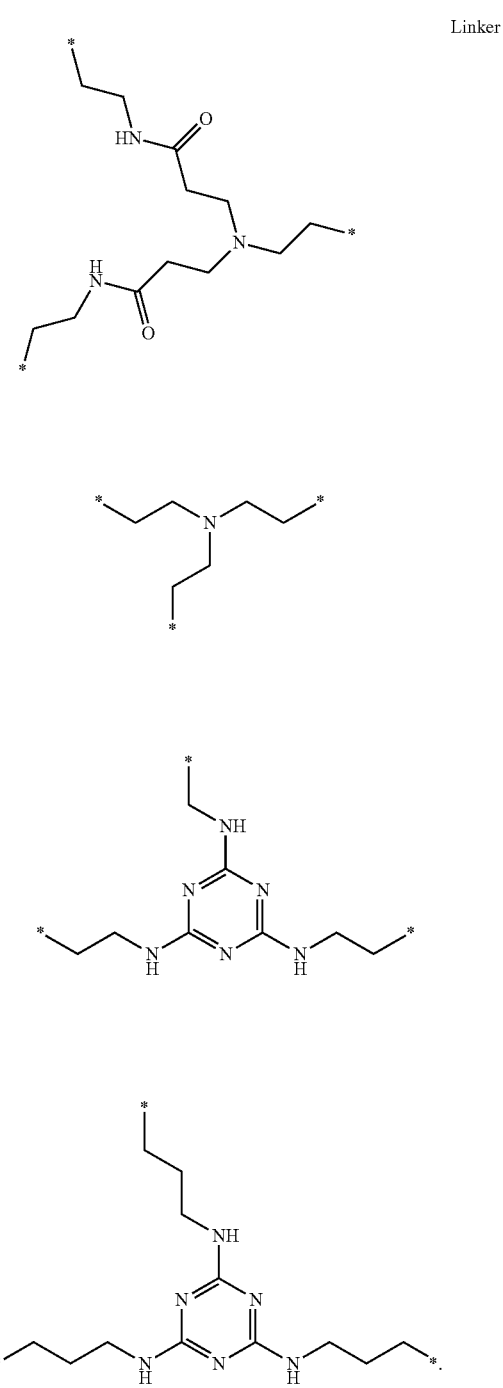

The preferred biocides of the present invention comprise tris-substituted biguanide compounds of the following formulas:

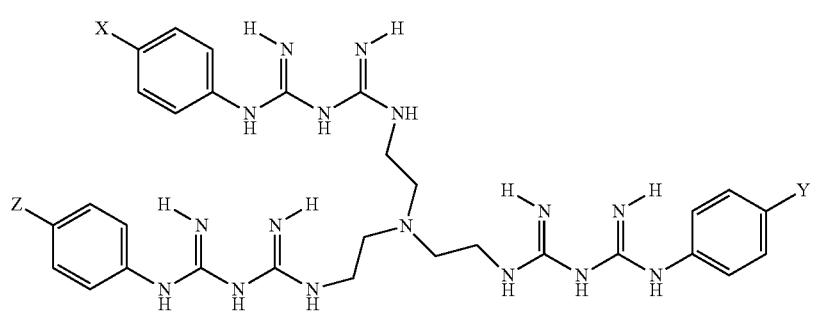

Formular 3

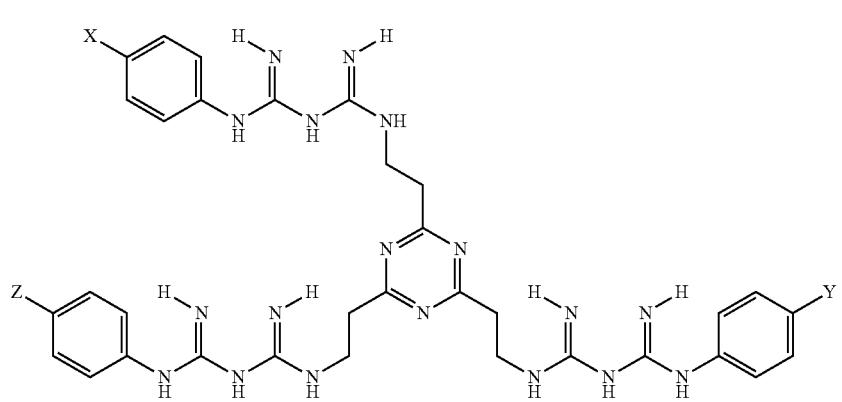

Formula 4 wherein X, Y, Z represent independently the same or different alkyl, O-alkyl, aryl or O-aryl groups, optionally substituted with halogen, O—R4, N—R5R6, R7; R4, R5, R6, R7 represent independently the same or different alkyl or aryl groups, optionally substituted with halogen, O-alkyl.

The preferred branched units of the present invention are exampled in but not limited to the following examples;

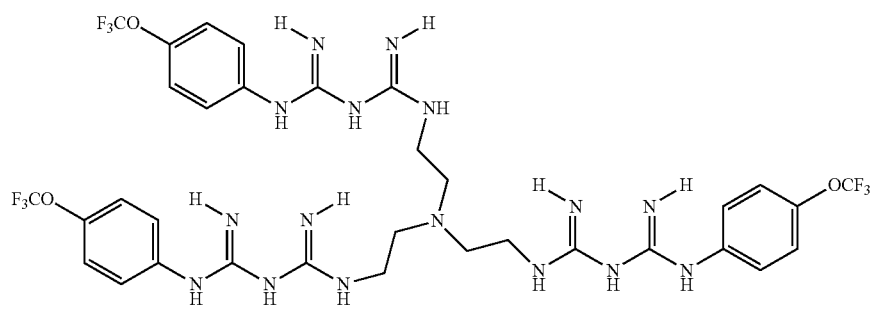

Example 1

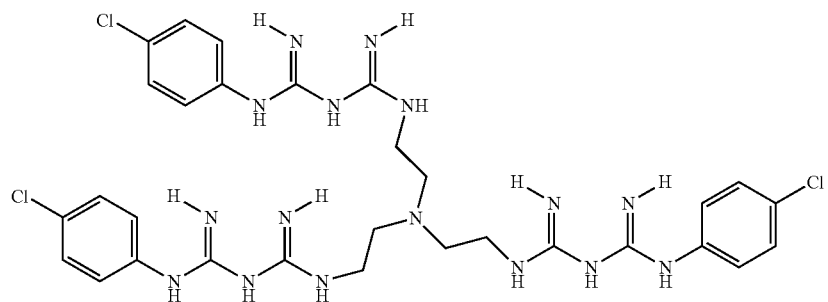

Example 2

-continued

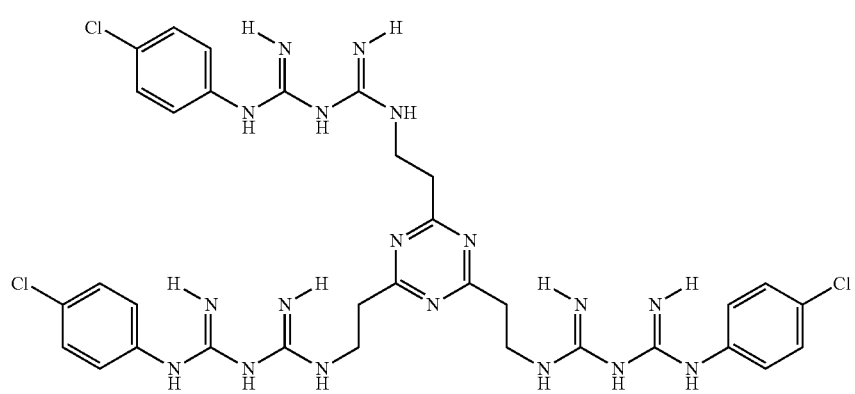

The biocides of the present invention have broad spectrum of antimicrobial activity and can be used in many applications including cosmetic products and ophthalmic solutions. The ophthalmic solutions of the present invention can be formulated in various compositions, particularly as disinfectants in contact lens care products and as preservatives in cosmetic, ophthalmic, nasal or otic compositions, and are especially suitable for use in ophthalmic compositions such as artificial tears or topical ophthalmic pharmaceutical preparations. The types of compositions which may be preserved by the compounds of formula (I) include: ophthalmic pharmaceutical compositions, such as those described below; otic pharmaceutical compositions, such as topical compositions used in the treatment of bacterial infections or inflammation of the ear; dermatological compositions, such as anti-inflammatory compositions, as well as shampoos and other cosmetic compositions; and various other types of pharmaceutical compositions. In general, the tris-substituted biguanides of the present invention will be present in the compositions at a concentration between about 0.00001 and 1.0 percent by weight/volume percent (w/v %). If used as a disinfectant, the tris-substituted biguanides are preferably present at a concentration of between about 0.0005 and 0.5 w/v %; if used as a preservative; the tris-substituted biguanides are present at a concentration between about 0.00005 and 0.05 w/v %. It is preferred that the tris-substituted biguanides are present at a concentration of between 0.001 and 0.05 w/v % if used as a disinfectant and between 0.0001 and 0.01 w/v % if used as a preservative.

The compositions of the present invention may additionally contain other components, for example, buffers, tonicity adjusting agents, chelating agents, surfactants, solubilizers, active pharmaceutical agents, preservatives, pH adjusting agents and carriers.

In the case of contact lens and ophthalmic solutions, for example, various agents are added to enhance compatibility with the eye. To avoid stinging or irritation it is important that the solution possess a tonicity and pH within the physiological range, e.g., 200-350 mOsmole for tonicity and 6.5-8.5 for pH. To this end, various buffering and osmotic agents are often added. The simplest osmotic agent is sodium chloride since this is a major solute in human tears. In addition propylene glycol, lactulose, sorbitol, mannitol or other osmotic agents may also be added to replace some or all of the sodium chloride. Also, various buffer systems such as citrate, phosphate (appropriate mixtures of $Na_2HPO_4$, $NaH_2PO_4$, and $KH_2PO_4$), borate (boric acid, sodium borate, potassium tetraborate, potassium metaborate and mixtures), bicarbonate, and tromethamine and other appropriate nitrogen-containing buffers (such as ACES, BES, BICINE, BIS-Tris, BIS-Tris Propane, HEPES, HEPPS, imidazole, MES, MOPS, PIPES, TAPS, TES, Tricine) can be used to ensure a physiologic pH between about pH 6.5 and 8.5. Borate and polyol systems may also be used to provide buffering, to enhance antimicrobial activity, or to provide both buffering and an enhancement of antimicrobial activity, or other useful properties to the compositions of the invention. The borate and polyol systems, which may be used, include those described in U.S. Pat. Nos. 6,849,253; 6,503,497; 6,365,636; 6,143,799; 5,811,466; 5,505,953; and 5,342,620; the entire contents of each are hereby incorporated into the present specification by reference.

The borates, which may be used in the compositions of the present invention, include boric acid and other pharmaceutically acceptable salts such as sodium borate (borax) and potassium borate. As used herein, the term "borate" refers to all pharmaceutically suitable forms of borates, as well as metaborates. Borates are common excipients in ophthalmic formulations due to good buffering capacity at physiological pH and well-known safety and compatibility with wide range of drugs and preservatives.

In addition to the compounds of formula (1, 2, 3, and 4) described above, the compositions of the present invention may contain one or more additional antimicrobial agent. The invention is not limited relative to the types of additional antimicrobial agent that may be utilized. The preferred biocides include:

polyhexamethylene biguanide ("PHMB"), polyquaternium-1, and the amino biguanides described in U.S. Pat. No. 6,664,294, the entire contents of which are hereby incorporated in the present specification by reference.

Amidoamines, amino alcohols, and borate/polyol complexes may also be utilized to enhance the antimicrobial activity of the compositions described herein. The preferred amidoamines are myristamidopropyl dimethylamine ("MAPDA") and related compounds described in U.S. Pat. No. 5,631,005 (Dassanayake, et al.). The preferred amino alcohols are 2-amino-2-methyl-1-propanol ("AMP") and other amino alcohols described in U.S. Pat. No. 6,319,464 (Asgharian). The entire contents of the '005 and '464 patents are hereby incorporated in the present specification by reference.

The following schemes further illustrate certain embodiments of the invention. These examples are provided to aid in the understanding of the invention and are not to be construed as limitations thereof.

Example 3

Scheme 1
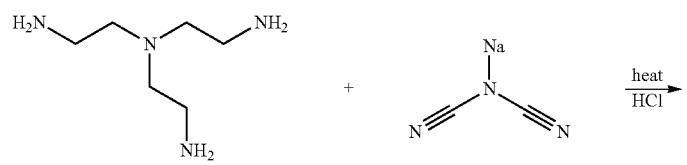
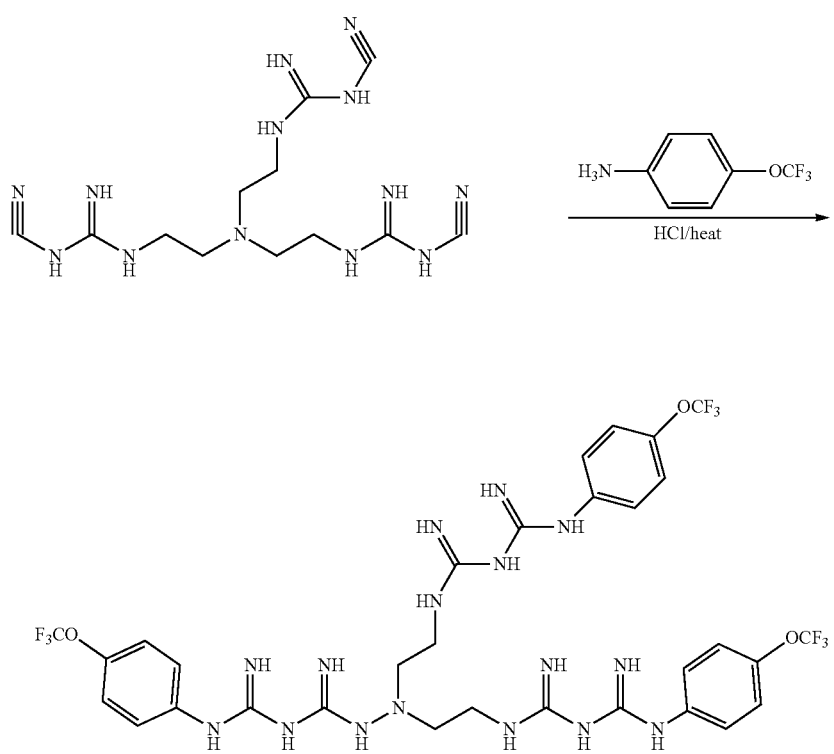
Scheme 2
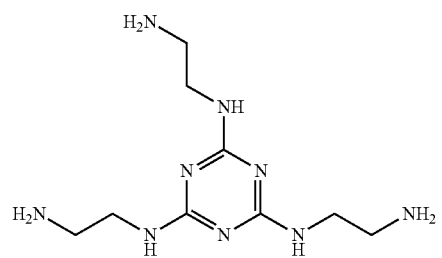
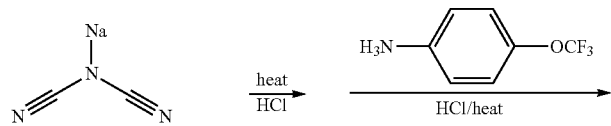

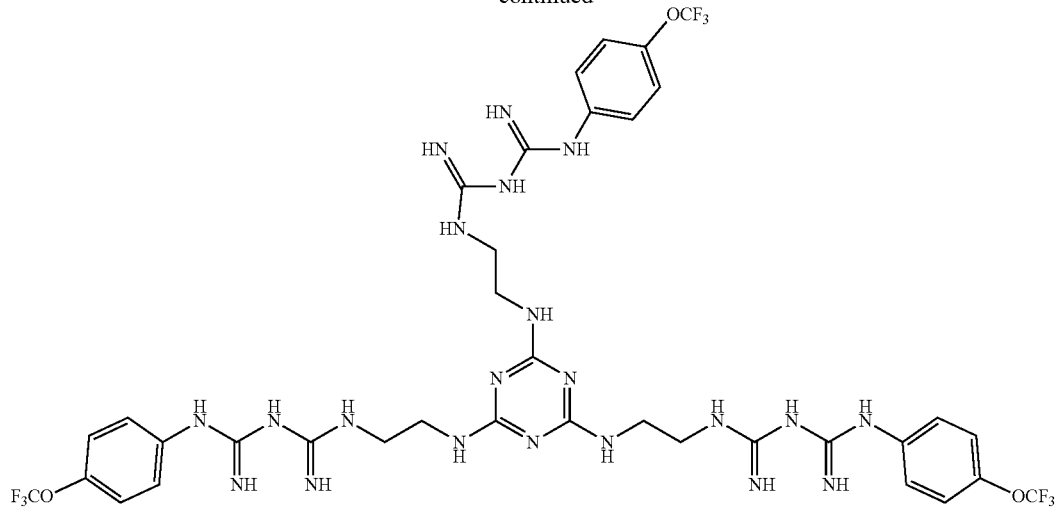

The compounds of the formula 1, 2, 3, and 4 were prepared using synthetic methods disclosed in the prior art.

Compound 1 (USD-18). Reaction of sodium dicyanamide with $N^1,N^1$-bis(2-aminoethyl)ethane-1,2-diamine (tri(2-aminoethyl)amine) and concentrated HCl in alcohol at 80-130° C. for 8-24 h gave the intermediate, tris(($N^3$-cyano-$N^1$-guanidino)ethyl)amine after purification. LCMS 248 (M+1). Reaction of tris(($N^3$-cyano-$N^1$-guanidino)ethyl)amine and 4-chloroaniline hydrochloride in alcohol at 80-150° C. for 2-8 h gave a white precipitate that was purified to give the desired compound as a white solid. NMR (CD$_3$OD/D$_2$O) □□7.10 (d, J=6 Hz, 6H), 7.01 (d, J=6 Hz, 6H), 4.91 (bs, 3H), 2.73 (bs, 6H), 2.08 (bs, 6H). □

Compound 2 (USD-19). Using the same procedure above and 4-trifluoromethylaniline hydrochloride the desired compound 2 was prepared as an off-white solid. NMR (DMSO/D2O) d 7.41 (bd, 6H), 7.30 (d, J=6 Hz, 6H), 3.25 (bs, 6H), 2.55 (bs, 6H).

Compound 3 (USD-39). Using the same procedure as in the preparation of Compound 1 and $N^1$, $N^1$-bis(3-aminopropyl)propane-1,3-diamine the desired Compound 3 was prepared as an off-white solid.

Compound 4 (USD-40). Using the same procedure above and 4-trifluoromethylaniline hydrochloride the desired Compound 4 was prepared as an off-white solid.

Compound 5 (USD-42). Using the same procedure as in the preparation of Compound 1 and $N^1$, $N^1$-bis(2-aminoethyl)propane-1,3-diamine the desired Compound 5 was prepared as an off-white solid.

Compound 6 (USD-45). Using the same procedure above and 4-trifluoromethylaniline hydrochloride the desired Compound 6 was prepared as an off-white solid.

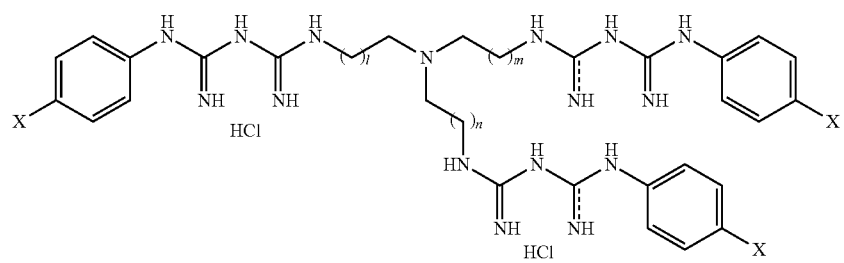

USD-18 X = Cl l, m, n = 0
USD-19 X = CF$_3$ l, m, n = 1
USD-39 X = Cl l, m, n = 1
USD-40 X = CF$_3$ l, m, n = 1
USD-42 X = Cl l, m = 0, n = 1
USD-45 X = CF$_3$ l, m = 0, n = 1

Compound 7 (USD-20). This is the reference compound (chlorhexidine dihydrochloride, CHX) and was obtained from Sigma-Aldrich.

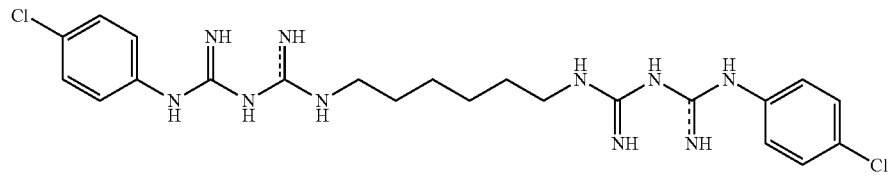

USD-20 Chlorhexidine (CHX)

The antibacterial effectiveness testing was run against 7 strains of bacteria using the following protocol.

Protocol: In 96 well polystyrene plates, compounds (USD-18, 19, 39, 40, 42, 45, and 20) are added using serial dilution method (0.19 mg/mL-100 mg/L) in brain heart infusion (BHI) broth media (containing acetic acid/BSA or not containing acetic acid/BSA*). Bacteria (either *E. coli* or *P. aeruginosa* or *S. aureus* or *S. marcenes* or *K. pneumonia* or *A. baumanni* or *C. albicans*) are added to all well except the control and incubated at 37° C. for 24 h. The absorbance was read at 600 nm.

MIC90 was calculated as the concentration at which ~90% growth inhibition is noticed. N=4 replicates for each compound and bacteria.

| Compound ID | μg/ML | Beginning concentration | $MIC_{90}$ (*P. aeruginosa*, ATCC-9027) in μg/mL | $MIC_{90}$ (*E. coli*, ATCC-8739) in μg/mL | MIC (*S. aeureus*, ATCC 6538) in μg/mL | MIC (*S. marcenes*, ATCC-21639) in μg/mL | MIC (*K. pneumonia*, ATCC-18804) in μg/mL | MIC (*A. baumanni-* ATCC-19606) in μg/mL | MIC (*C. albicans*, ATCC1-0231) in μg/mL |
|---|---|---|---|---|---|---|---|---|---|
| USD 18* | 1000 | suspension | 6.25 | 3.12 | 0.78 | 3.12 | | 3.12 | |
| USD 19* | 1000 | suspension | 12.5 | 12.5 | 3.12 | 3.12 | | 3.12 | |
| USD 20* | 1000 | suspension | 25 | 0.78 | 0.78 | 6.25 | 25 | 25 | |
| USD 18 | 1000 | suspension | 0.76 | 3.15 | 0.76 | 50 | 12.5 | 6.25 | 6.25 |
| USD 19 | 1000 | suspension | 3.15 | 315 | 1.5 | 100 | 25 | 1.5 | 6.25 |
| USD 18 | 1000 | in DMSO/Water | 0.76 | 6.25 | 0.76 | 12.5 | 6.25 | 0.39 | 3.12 |
| USD 20 | 1000 | in DMSO/Water | 1.5 | 1.5 | 0.76 | 3.25 | 3.12 | 0.39 | 12.5 |
| USD 39 | 1000 | soluble in water | 3.125 | | | | 50 | 12.5 | |
| USD 40 | 1000 | soluble in water | 3.125 | | | | | 12.5 | 12.5 |
| USD 42 | 1000 | soluble in water | 3.125 | | | | | 12.5 | 6.25 |
| USD 45 | 1000 | soluble in water | 6.25 | | | | | 6.25 | 6.25 |

What is claimed is:

1. A biocide solution comprising a compound having three substituted biguanide groups of the following formula:

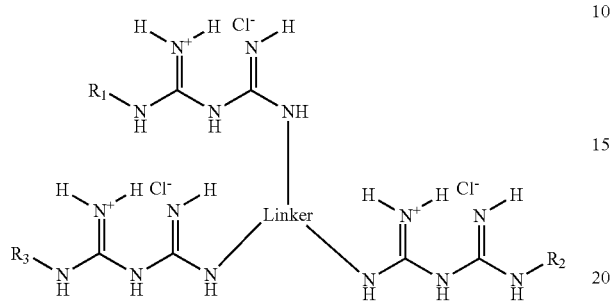

Formula 1 wherein Linker represents linkage group with 3 or more points of connections for biguanide groups and;

R1, R2, R3 represent independently the same or different alkyl, aryl or heterocyclic groups, optionally substituted with halogen, O—R4, N—R5R6, R7;

R4, R5, R6, R7 represent independently the same or different alkyl or aryl groups, optionally substituted with halogen, O-alkyl;

Cl⁻ represent counter ions including chloride, bromide, iodide, acetate, or gluconate.

2. The biocide solution according to claim 1 comprising a compound having three substituted biguanide groups of the following formula:

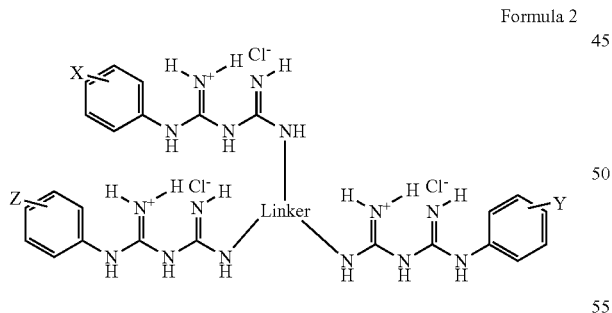

Formula 2 wherein Linker represent linkage group with 3, or more points of connections for biguanide groups;

X, Y, Z represent independently the same or different alkyl, O-alkyl, aryl or O-aryl groups, optionally substituted with halogen, O—R4, N—R5R6, R7;

R4, R5, R6, R7 represent independently the same or different alkyl or aryl groups, optionally substituted with halogen, O-alkyl; and the Linker represents linkage groups of the following structures

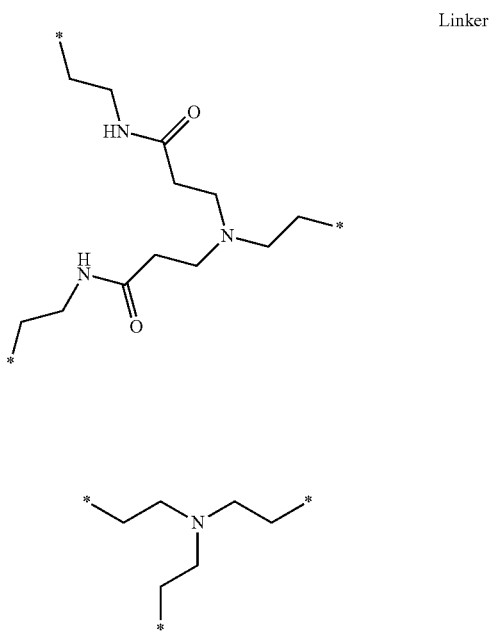

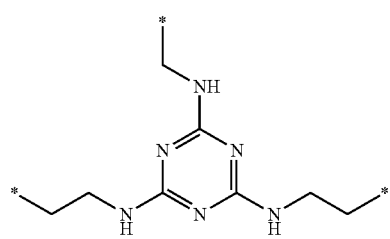

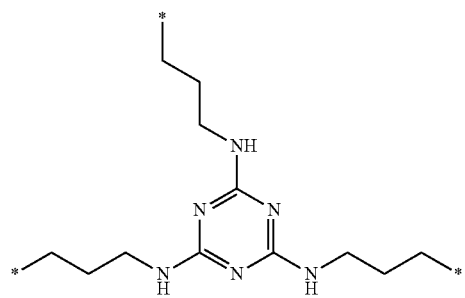

wherein Cl⁻ represent counter ions including chloride, bromide, iodide, acetate, or gluconate.

3. The biocide solution according to claim 2 wherein the compound has three substituted biguanide groups of the following formula:

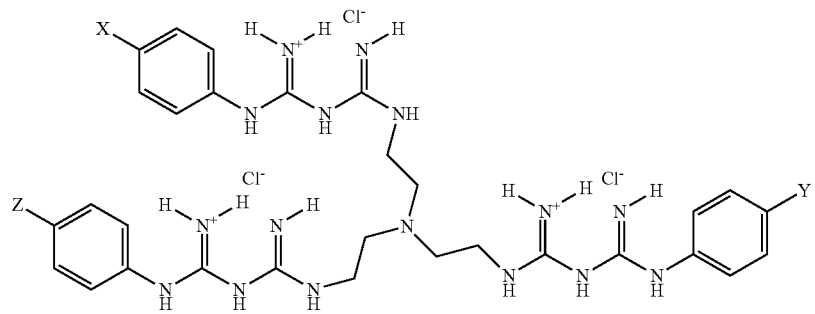

Formula 3

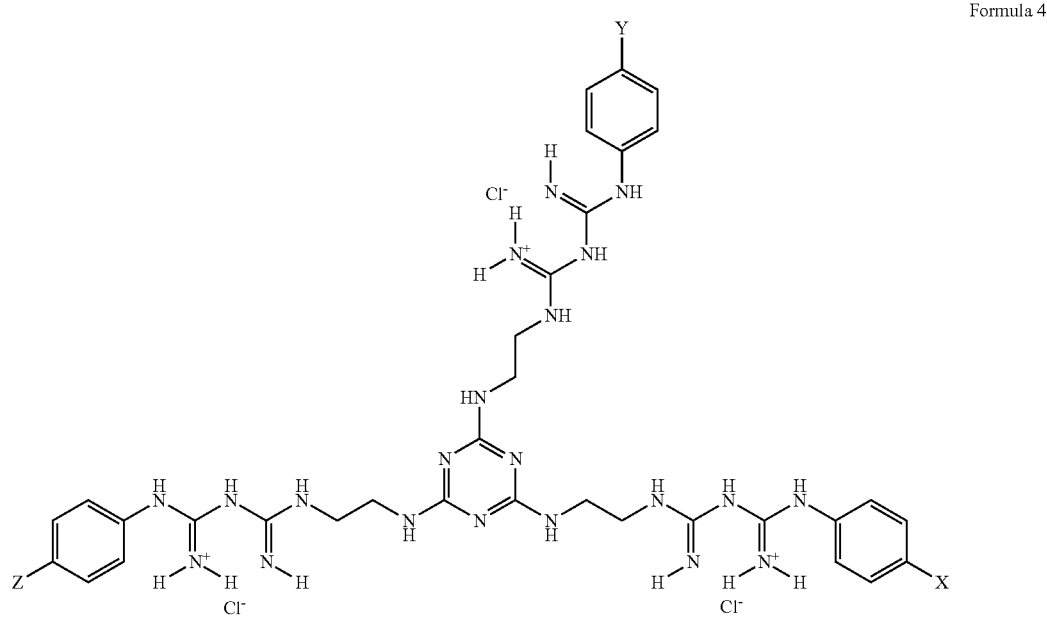

Formula 4 wherein X, Y, Z represent independently the same or different alkyl, O-alkyl, aryl or O-aryl groups, optionally substituted with halogen, O—R4, N—R5R6, R7;
R4, R5, R6, R7 represent independently the same or different alkyl or aryl groups, optionally substituted with halogen, O-alkyl; and
Cl⁻ represent counter ions including chloride, bromide, iodide, acetate, or gluconate.

4. The biocide solution according to claim 1, comprising a preservation-effective amount of a compound for a pharmaceutical composition.

5. The biocide solution according to claim 2, comprising a preservation-effective amount of a compound for a pharmaceutical composition.

6. The biocide solution according to claim 1, comprising a disinfecting-effective amount of a compound for a lens care composition.

7. The biocide solution according to claim 2, comprising a disinfecting-effective amount of a compound for a lens care composition.

8. The biocide solution of claim 2, wherein the composition may contain one or more additional antimicrobial agents selected from polyhexamethylene biguanide polymers ("PHMB"), polyquaternium-1, myristamidopropyl dimethylamine, and the amino biguanides.

9. The biocide solution of claim 2, wherein the concentration of the compound in an ophthalmic solution ranges from 0.0001 to 5.0 w/v %.

10. The biocide solution according to claim 1 comprising a preservation-effective amount of a compound for a mouth wash composition.

11. The biocide solution according to claim 2 comprising a preservation-effective amount of a compound for a mouth wash composition.

12. A method for preparation of a compound according to claim 2 by a process of:
   a) condensation of sodium dicyanamide and a trifunctional primary amine,
   b) reaction with anilines hydrochloride,
      wherein trifunctional primary amine is selected from the groups consisting of propane-1,2,3-triamine, pentane-1,3,5-triamine, $N^1,N^1$-bis(2-aminoethyl)-ethane-1,2-daiamine, $N^2,N^4,N^6$-tris(6-aminohexyl)-1,3,5-triazine-2,4,6-triamine, $N^2,N^4,N^6$-tris(6-aminopropyl)-1,3,5-triazine-2,4,6-triamine, $N^2,N^4,N^6$-tris(6-aminobutyl)-1,3,5-triazine-2,4,6-triamine, $N^2,N^4,N^6$-tris(6-aminoheptyl)-1,3,5-triazine-2,4,6-triamine, $N^2,N^4,N^6$-tris(6-aminopentyl)-1,3,5-triazine-2,4,6-triamine.

13. A method for preparation of a compound according to claim 2 by a process of:
   a) condensation of sodium dicyanamide and anilines hydrochloride,
   b) reaction with a trifunctional primary amine and acid,
      wherein trifunctional primary amine is selected from the groups consisting of propane-1,2,3-triamine, pentane-1,3,5-triamine, N¹,N¹-bis(2-aminoethyl)-ethane-1,2-daiamine, N²,N⁴,N⁶-tris(6-aminohexyl)-1,3,5-triazine-2,4,6-triamine, N²,N⁴,N⁶-tris(6-aminopropyl)-1,3,5-triazine-2,4,6-triamine, N²,N⁴,N⁶-tris(6-aminobutyl)-1,3,5-triazine-2,4,6-triamine, N²,N⁴,N⁶-tris(6-aminoheptyl)-1,3,5-triazine-2,4,6-triamine, N²,N⁴,N⁶-tris(6-aminopentyl)-1,3,5-triazine-2,4,6-triamine.

14. The biocide solution according to claim 2 comprising a compound including at least one of the following chemicals:

Formula 5

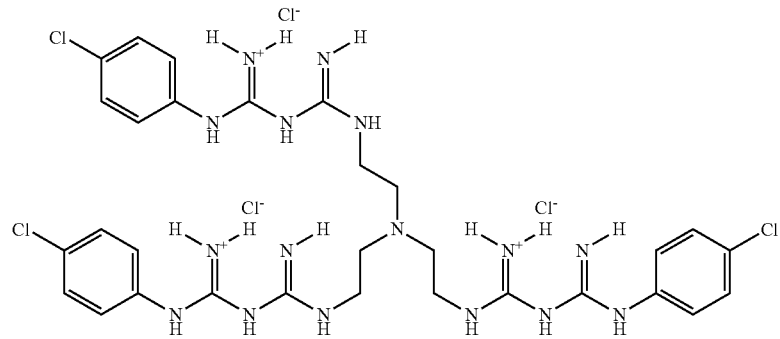

Formula 6

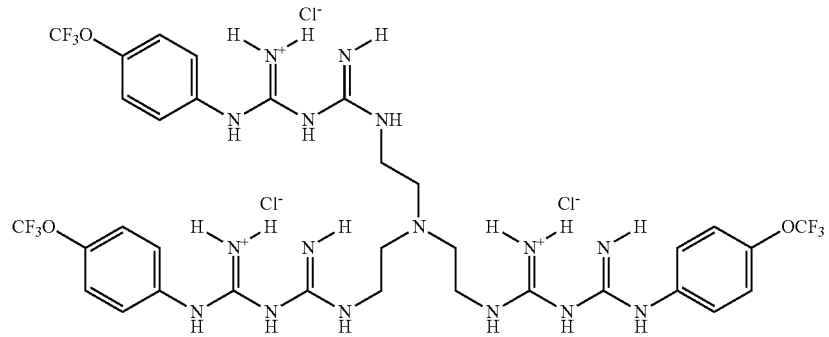

Formula 7

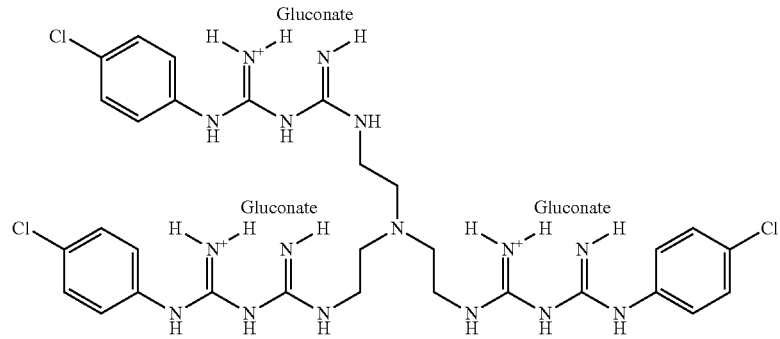

Formula 8
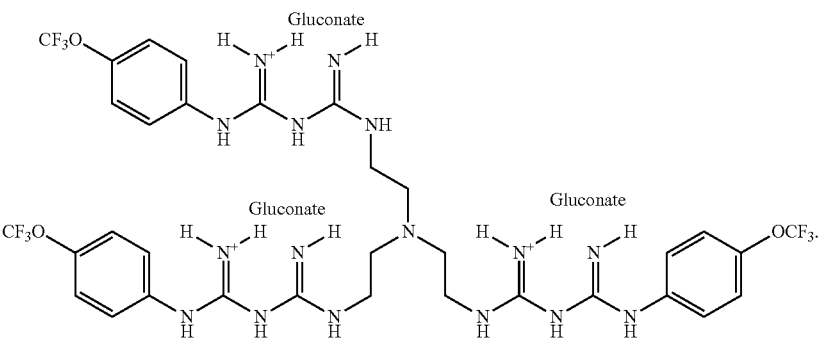
* * * * *